US010624813B2

(12) United States Patent
Monterenzi

(10) Patent No.: US 10,624,813 B2
(45) Date of Patent: Apr. 21, 2020

(54) METHOD AND DEVICE FOR THE DISPENSATION OF MISTS FOR THERAPEUTIC USE

(71) Applicant: Roberto Monterenzi, Massagno (CH)

(72) Inventor: Roberto Monterenzi, Massagno (CH)

( * ) Notice: Subject to any disclaimer, the term of this patent is extended or adjusted under 35 U.S.C. 154(b) by 298 days.

(21) Appl. No.: 15/517,877

(22) PCT Filed: Oct. 8, 2014

(86) PCT No.: PCT/IT2014/000264
§ 371 (c)(1),
(2) Date: Apr. 7, 2017

(87) PCT Pub. No.: WO2016/056033
PCT Pub. Date: Apr. 14, 2016

(65) Prior Publication Data

US 2017/0246080 A1 Aug. 31, 2017

(51) Int. Cl.
*A61H 33/06* (2006.01)
*A61M 11/02* (2006.01)
(Continued)

(52) U.S. Cl.
CPC ......... *A61H 33/066* (2013.01); *A61G 10/005* (2013.01); *A61G 10/02* (2013.01);
(Continued)

(58) Field of Classification Search
CPC ......... A62B 31/00; A62B 17/00; A62B 29/00; A62B 33/00; E04H 15/14; E04H 15/20; E04H 15/22; E04H 15/405; E04H 15/425; E04H 15/44; E04H 15/46; A61M 11/00; A61M 11/02; A61M 15/00; A61M 15/02; A61M 16/00; A61M 16/0057; A61M 16/0066; A61M 16/0627; A61M 16/10; A61M 16/14; A61M 35/00; A61M 2202/064; A61M 2209/06; A61M 2240/00; A61M 2250/00; A61M 21/0094;
(Continued)

(56) References Cited

U.S. PATENT DOCUMENTS 2,297,150 A * 9/1942 Hunter .................... E04H 15/20
135/906
2,915,074 A * 12/1959 Cameto .................. A61G 10/04
52/2.21

(Continued)

*Primary Examiner* — Joseph D. Boecker
(74) *Attorney, Agent, or Firm* — Pearne & Gordon LLP

(57) ABSTRACT

A device and associated method for the dispensation of mists for therapeutic use, comprising: a dispensing member (2) for dispensing an air flow (3) within which micronized particles of a liquid or solid therapeutic substance are dispersed; a chamber (11) having at least one inlet (12) for said air flow (3) generated by the dispensing member (2) and at least one outlet (13) for said air flow (3) present inside the chamber (11) itself; and a communication conduit (10) interposed between said dispensing member (2) and said chamber (11) in order to introduce the air flow (3) into the chamber (11) itself; said chamber (11) being switchable between an operative condition of maximum volume in which it internally defines a space (20) for containing at least one user, and a non-operative condition of minimum volume suitable for transport and/or storage.

10 Claims, 4 Drawing Sheets

(51) Int. Cl.

| | |
|---|---|
| ***A61M 35/00*** | (2006.01) |
| ***A61M 11/00*** | (2006.01) |
| ***A61G 10/00*** | (2006.01) |
| ***A61M 16/06*** | (2006.01) |
| ***A61G 10/02*** | (2006.01) |
| ***A61M 15/00*** | (2006.01) |
| ***A61M 15/02*** | (2006.01) |
| ***A61M 16/14*** | (2006.01) |
| *A61H 33/04* | (2006.01) |
| *A61M 16/00* | (2006.01) |

(52) U.S. Cl.
CPC ............ *A61M 11/00* (2013.01); *A61M 11/02* (2013.01); *A61M 15/0065* (2013.01); *A61M 15/02* (2013.01); *A61M 16/0627* (2014.02); *A61M 16/14* (2013.01); *A61M 35/00* (2013.01); *A61H 2033/048* (2013.01); *A61H 2201/0103* (2013.01); *A61H 2201/0161* (2013.01); *A61M 16/0066* (2013.01); *A61M 2202/064* (2013.01); *A61M 2209/06* (2013.01)

(58) Field of Classification Search
CPC ...... A61G 10/00; A61G 10/005; A61G 10/02; A61G 10/023; A61G 10/026; A61G 10/04; A61G 11/00; F24F 2221/12
See application file for complete search history.

(56) References Cited

U.S. PATENT DOCUMENTS

| | | | | | | |
|---|---|---|---|---|---|---|
| 3,703,173 | A | * | 11/1972 | Dixon | A61G 10/04 | 128/200.14 |
| 4,590,956 | A | * | 5/1986 | Griesenbeck | E04H 15/40 | 135/116 |
| 5,245,998 | A | * | 9/1993 | Sundsrud | A61G 10/04 | 128/200.24 |
| 5,360,001 | A | * | 11/1994 | Brill | A61G 10/026 | 128/202.12 |
| 5,495,857 | A | * | 3/1996 | Fegan | A61G 10/02 | 128/848 |
| 5,832,919 | A | * | 11/1998 | Kano | A61G 10/005 | 128/205.26 |
| 7,481,234 | B1 | | 1/2009 | Gustafson et al. | | |
| 2010/0233019 | A1 | * | 9/2010 | Al-Thallab | A61L 9/20 | 422/4 |
| 2011/0132420 | A1 | * | 6/2011 | Livacich | E04H 15/001 | 135/123 |
| 2011/0253802 | A1 | * | 10/2011 | Freelove | B05B 1/14 | 239/69 |
| 2016/0074268 | A1 | * | 3/2016 | Breegi | A61G 10/005 | 600/21 |

* cited by examiner

METHOD AND DEVICE FOR THE DISPENSATION OF MISTS FOR THERAPEUTIC USE

The present invention relates to a device and associated method for the dispensation of mists for therapeutic and non-therapeutic use, for example for halotherapy treatments.

As is well known, a mist for therapeutic use consists in the dispensation by inhalation of a liquid or solid medical or non-medical substance, which is preferably micronized and rendered volatile within an air flow.

Typically, in order to favour intake of the medicinal substance through the breathing passages use is made of masks and specific conduits that aim the volatile substance directly at the user's nose and/or mouth.

As is well known, the masks are applied on the user's face and held in place in the area surrounding the nose and mouth either by hand or by means of specific elastic bands that fit around the user's head. There are also known conduits designed to be brought near by hand, and likewise held by hand in front of the user's nostrils.

The mist dispensation devices summarily described above have some major drawbacks, however.

In fact, it should be considered that applying the mask is often complicated and inefficient, especially in the case of patients who must endure the presence of the mask on their face. For example, in the case of children or infants, it is particularly complicated to apply the mask and hold the conduits in place in front of the breathing passages.

Moreover, the manual application of such devices is not always done correctly, causing partial dispensation of the medical substance with consequent limitations in terms of efficiency.

Another problem encountered in the use of such devices is the size of the particles, which in most cases are not smaller than 10 microns, and thus not usable for mists.

There are also known devices for the dispensation of mists used, for example, in halotherapy, which involve conditioning the atmosphere surrounding the user.

In particular, halotherapy consists in the dispensation by inhalation of micronized medical sodium chloride distributed inside a confined environment, recommended for its therapeutic effects, for example in the treatment of bronchopulmonary diseases and skin pathologies. It should be specified that the expression "micronized medical salt" means sodium chloride suitable for use in medical therapies and finely pulverized into particles having a size, for example, of between 0.2 and 10 micrometres. In this case, the confined environment is defined by a closed chamber (salt cave), constructed specifically to accommodate the user and in which the micronized salt is diffused.

To avoid saturation of the chamber and thus to maintain a controlled environment inside it, forced air circulation systems are provided.

Such devices assure correct inhalation of the therapeutic substance (micronized salt) also by patients for whom applying the above-mentioned masks is complicated. Moreover, considering the beneficial effects of halotherapy on skin, the patient is completely enveloped by the micronized salt conveyed by the air flows generated by the forced circulation.

However, this type of device, too, has some major drawbacks, mostly tied to the structure of the chamber in which the therapeutic treatment is carried out.

The Applicant has in fact found that the known devices are characterized by a complex structure and/or a high cost of construction. This cost is determined by the need to set up a confined environment and thus to construct a closed chamber used exclusively for the dispensation of micronized salt. Moreover, the construction costs are particularly high also due to the characteristics of the building materials used (resistant to the corrosion caused by sodium chloride) and the presence of the necessary forced air circulating ventilation systems. In fact, in most cases the chambers are cube shaped and this prevents the air flow and sodium chloride from being diffused homogeneously. For this reason, use is made of ventilation systems adapted to homogeneously distribute the mist in the environment.

What is more, a closed chamber cannot be constructed in a home environment due to the obvious limitations tied to construction costs and space. Consequently, mist dispensing devices of this type are exclusively present in specialized clinics that have a sufficiently large space to contain the closed chamber.

In this situation, the object at the basis of the present invention, in the various aspects and/or embodiments thereof, is to provide a device for the dispensation of mists for therapeutic use that is able to remedy one or more of the aforementioned drawbacks.

In particular, it is an object of the present invention to provide a device and a method for the dispensation of mists for therapeutic use that is simple, with moderate costs and compact dimensions.

It is a further object of the present invention to provide a mist that is capable of dispensing in a correct manner, irrespective of the type of user (adult or child) and therapeutic substance.

A still further object of the present invention is to provide a device and associated method for the dispensation of mists for therapeutic use that can be used in a home environment, without necessarily having to set up a fixed structure.

These objects, and any other ones that will become more apparent in the course of the following description, are substantially achieved by a device, and associated method, for the dispensation of mists for therapeutic use according to one or more of the appended claims, each of which, taken on its own (without the associated depending claims) or in any combination with the other claims, as well as according to the following aspects and/or embodiments, variously combined, also with the aforesaid claims.

Additional features and advantages will become more apparent from the detailed description of some example but non-exclusive embodiments, including a preferred embodiment, of a device and associated method for the dispensation of mists for therapeutic use in accordance with the present invention. The description shall be set forth hereinbelow with reference to the appended drawings, provided solely by way of non-limiting illustration, in which.

With reference to the appended figures, the reference number 1 denotes overall a device for the dispensation of mists for therapeutic and non-therapeutic use.

It should be specified that the term mist refers to any type of mixture in which solid or liquid particles are dispersed in a gas (air).

The diameter of the particles, which constitute one or more therapeutic substances, is normally comprised between 0.2 and 10 micrometres.

The present invention has particular but not exclusive application in the realm of halotherapy for the dispensation of micronized medical sodium chloride distributed in a finely dispersed state. Halotherapy is particularly recommended for its therapeutic effects in the treatment of bronchopulmonary diseases and skin pathologies.

With reference to the appended figures, the device 1 comprises a member 2 for dispensing an air flow 3 within which the aforementioned micronized particles of a liquid or solid therapeutic substance (for example medical salt) are dispersed.

Figure 1:
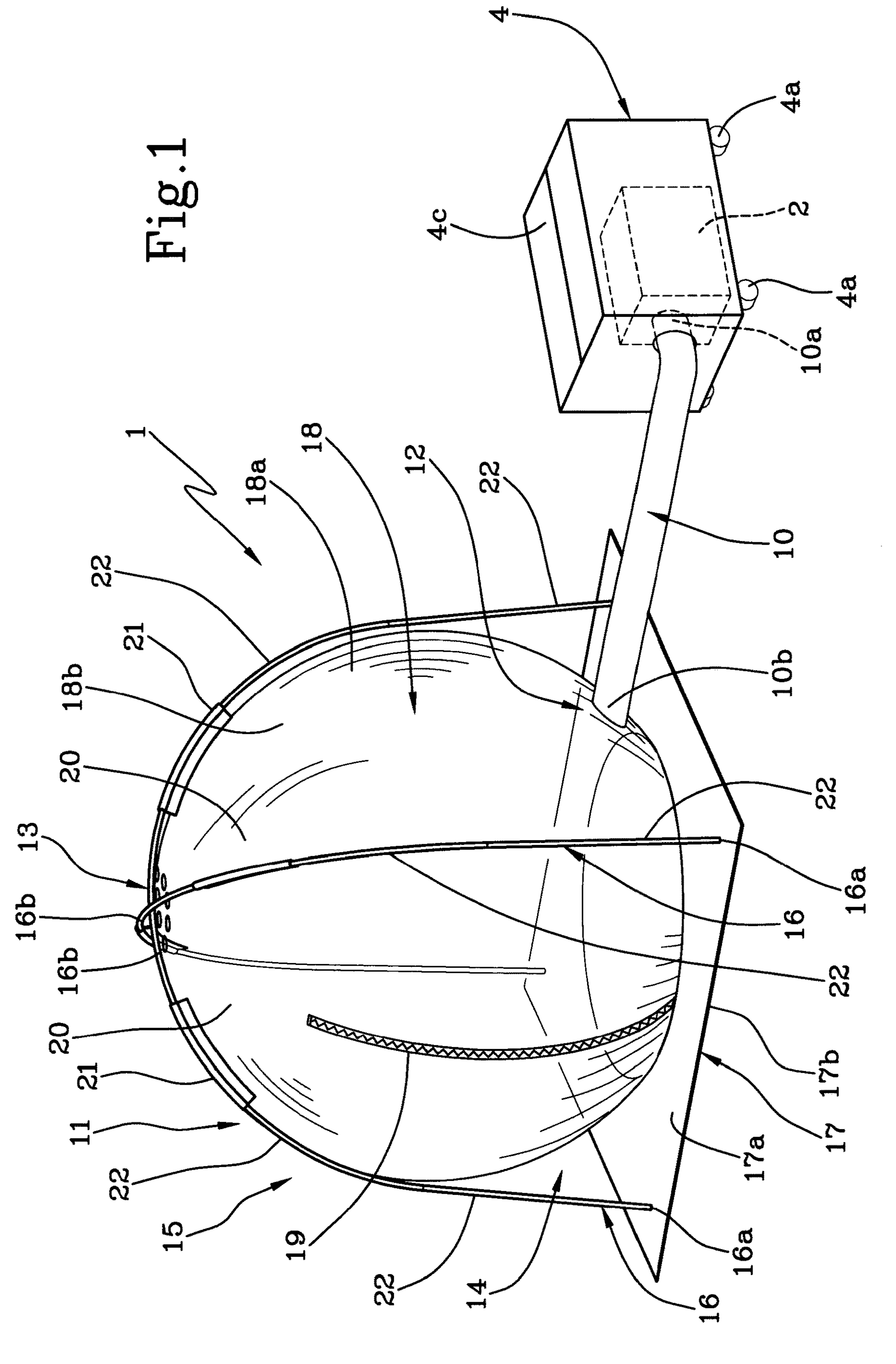
FIG. 1 is a perspective view of a device for the dispensation of mists for therapeutic use in a respective operating condition and in accordance with the present invention.
Figure 2:
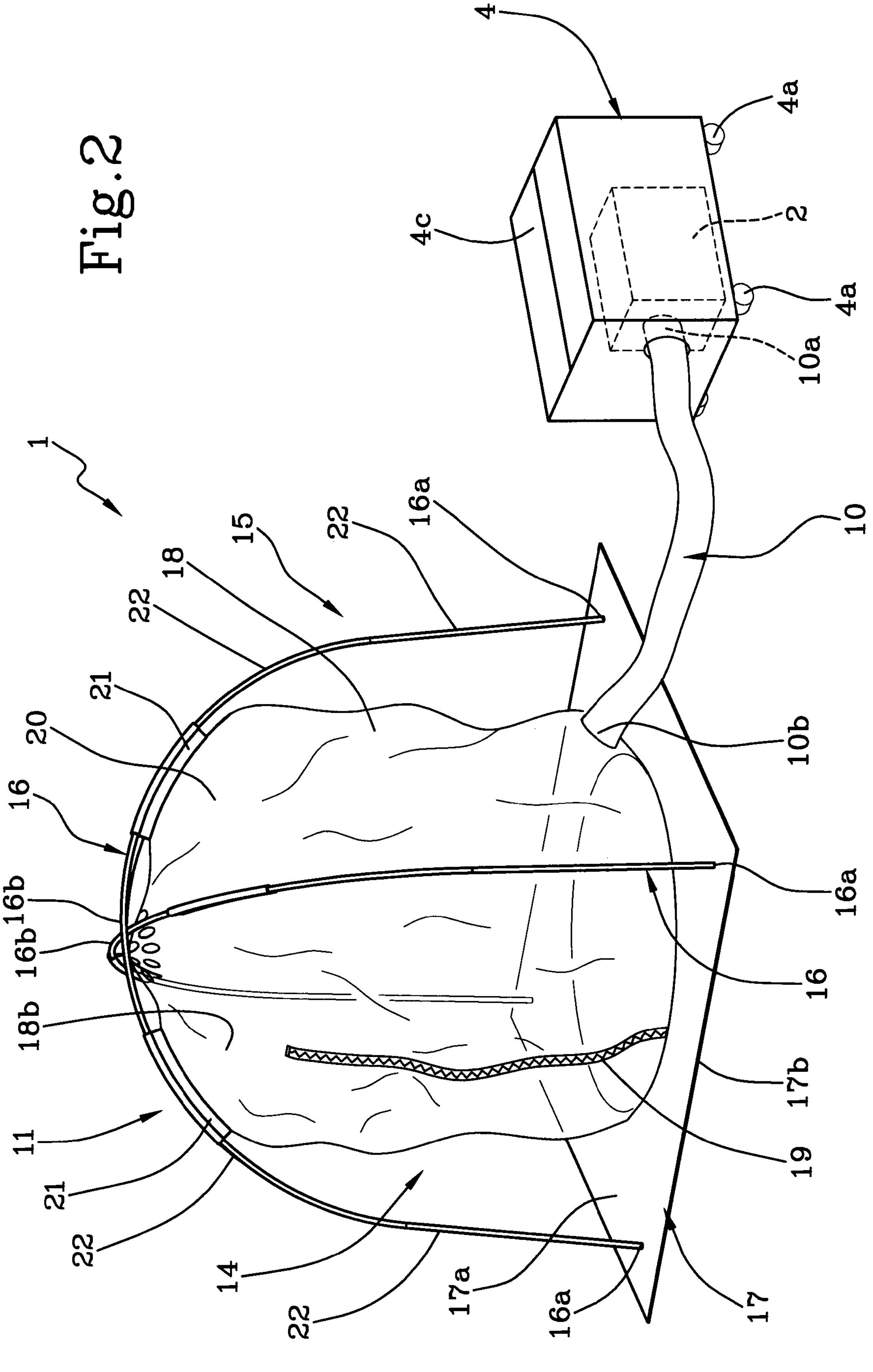
FIG. 2 is a perspective view of the device of FIG. 1 in a respective non-operating condition.
Figure 6:
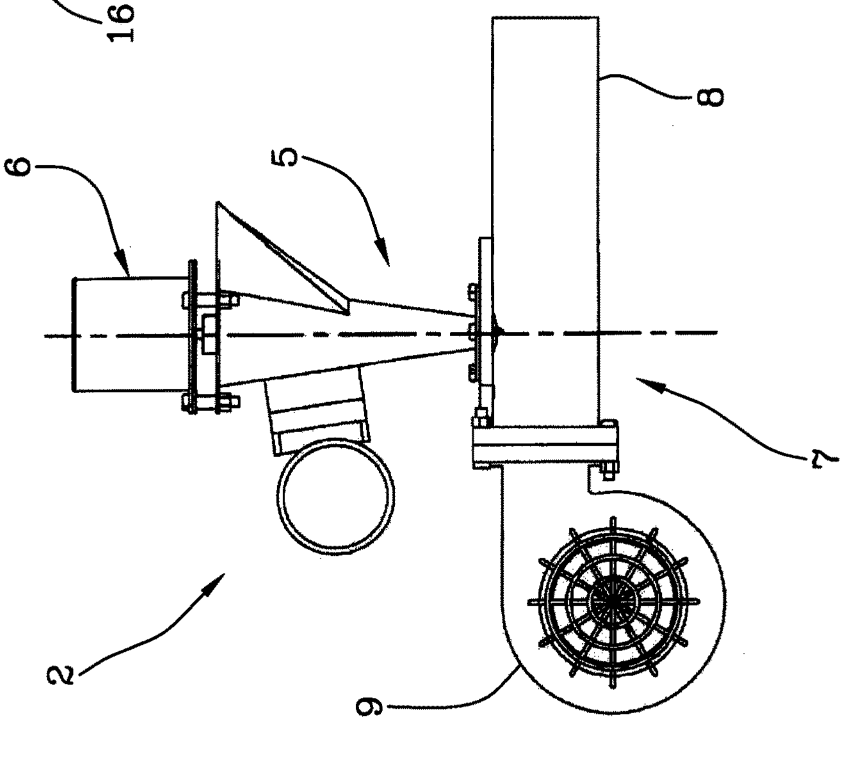
FIG. 6 is a schematized side elevation view of a constructive detail of the device of FIG. 1 in accordance with the present invention.

The dispensing member 2 is preferably contained in a respective box-like body 4 better described below in the present disclosure (FIGS. 1 and 2). The member 2 is illustrated, by way of example, in FIG. 6 in the form of an element for distributing micronized medical salt. In particular, the member 2 comprises a container 5 having a vertical longitudinal extent and a lower end portion that has a mouth for releasing the medical salt, the container 5 being configured to contain an amount of medical salt; a feed screw (not illustrated) inserted in the container 5 and rotation members 6 of the screw mechanically connected to the screw itself so as to set it into rotation relative to the container 5. The screw is configured to feed the medical salt downward along the longitudinal extent by its rotation, so that the medical salt is released in every other point of the container 5*a* in a manner that is controlled and sustained by the screw.

The member 2 further comprises a dispenser 7 comprising a dispensing conduit 8 and a ventilation member 9 for generating an air flow inside the dispensing conduit 8, where the medical salt is released by the screw directly into the aforesaid air flow and where the dispensing conduit 8 is configured in such a way that said air flow is substantially horizontal.

The micronized salt contained in the container 5 is then released into the treatment environment without undergoing any further step, for example a further micronization step. In other words, the medical salt is dispensed from above, by means of the screw, at a controlled dosage directly from the container 5 in a horizontal air flow, which is capable of conveying the medical salt from the dispensing conduit 8 toward the outside of the member 2 and diffusing it in the treatment environment.

In accordance with a further embodiment not illustrated in the appended figures, the screw can be positioned with a horizontal longitudinal extent (rotation axis). The screw thus transfers the micronized salt from a respective hopper, provided so as to receive the micronized salt coming from a container, toward the outlet of the ventilation unit. In this condition, the dispensing function remains identical to that of the solution with the vertical screw, with the sole difference that only the controlled feed of salt imposed by the rotation of the screw is exploited.

Owing to the fact that the device dispenses medical salt without employing a micronizer member, the micronized medical salt introduced into the container maintains its physical characteristics, for example its particle size composition, intact up until dispensation from the dispensing conduit. The position of the screw relative to the conduit 8 moreover enables the dispensed medical salt to be dosed with sufficient precision and/or the dosage (for example the mass concentration) to be varied.

Figure 5:
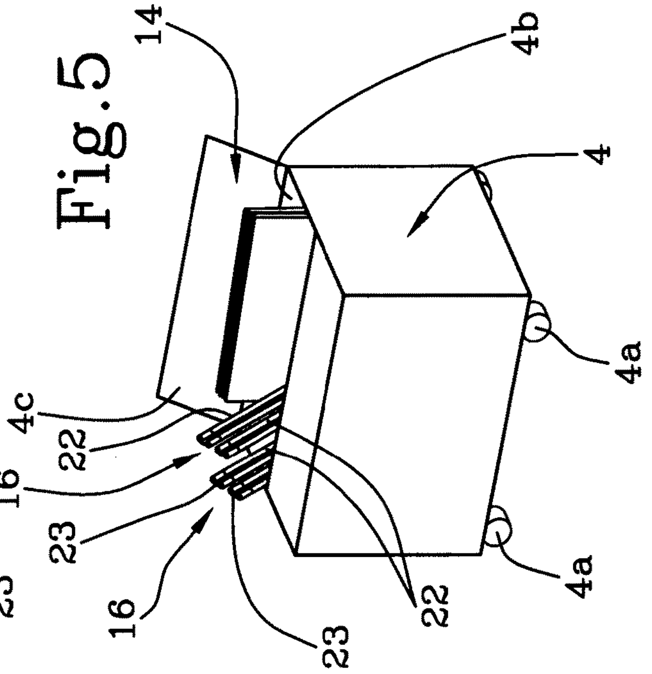

As specified above, the member 2 is contained and enclosed in a box-like body 4 that has an aperture for the passage of a communication conduit 10. The box-like body 4, which can have any shape and size, is preferably provided with a plurality of supporting wheels 4*a* to facilitate transport of the entire device 1. Moreover, the box-like body 4 comprises an internal area 4*b* for containing the entire device 1, accessible from the outside by means of a door 4*c* suitably hinged to the body 4 (FIG. 5).

The conduit 10 is made of deformable elastic material, preferably PVC, and has a first end 10*a* connected to the dispensing conduit 8 of the member 2 and a second end 10*b* connected to a chamber 11.

In greater detail, the communication conduit 10 is interposed between the dispensing member 2 and the chamber 11 so as to introduce into the chamber 11 itself the air flow 3 generated by the ventilation member 9 in which the particles of the therapeutic substance (micronized salt) are dispersed.

Moreover, the conduit 10 is envisaged so as to be switched into an operative condition of maximum volume in which it has a tubular profile to enable the passage of the air flow 3, and a non-operative condition of minimum volume in which it is folded up into a sheet and stored in the internal area 4*b* of the box-like body 4.

The chamber 11 has at least one inlet 12 for the air flow 3 generated by the dispensing member 2 and engaged with the conduit 10, and at least one outlet 13 for the air flow 3 present inside the chamber 11.

Advantageously, the chamber 11 can be switched between an operative condition of maximum volume (FIG. 1), in which it internally defines a space 20 for containing at least one user, and a non-operative condition of minimum volume (FIG. 4) suitable for transport and/or storage (FIG. 5).

Figure 4:
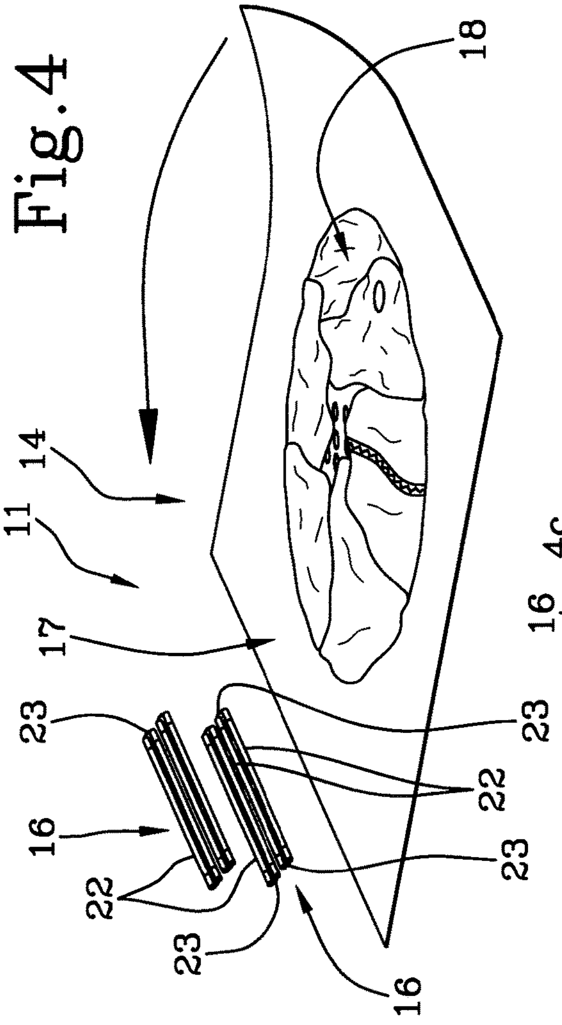
FIGS. 4 and 5 are perspective views of respective folding and storage phases of the device of FIG. 1.

In greater detail, the chamber 11 comprises: a body 14 made of flexible material, preferably PVC, and in the form of a sheet to be folded up in the non-operative condition (FIG. 5). The body 14, in the respective operative condition, is supported by a respective supporting frame 15, featuring a plurality of flexible poles 16, which can be folded up in the non-operative condition (FIGS. 4 and 5).

More in particular, the body 14 comprises a base 17 having the form of a sheet and configured to be rested upon the ground in the respective operative condition (FIGS. 1 and 2). The base 17 defines an upper rest surface 17*a* for the user, and a lower surface 17*b* in contact with the ground.

Extending from the upper surface 17*a* there is a lateral wall 18, made in one piece with said base 17, and having an outer surface 18*a* and an inner surface 18*b* defining, in cooperation with the upper surface 17*a* of the base 17, the space 20 for containing at least one user.

The lateral wall 18 is preferably made of transparent material to enable the passage of light into the space 20. Moreover, the lateral wall 18 is made of flexible material so as to inflate during the introduction of the air flow 17 generated by the member 2 (FIG. 1).

In accordance with a preferential, but non-limiting embodiment, the lateral wall 18 has a substantially spherical conformation in which the inlet 12 is defined by at least one through opening fashioned in an area of the lateral wall 18 near the base 17 (lower position). The outlet 13 is defined by least one through opening, preferably a plurality of through holes, made in an area of the lateral wall 18 that is distal relative to the base and corresponds to the top of the spherical conformation.

Figure 3:
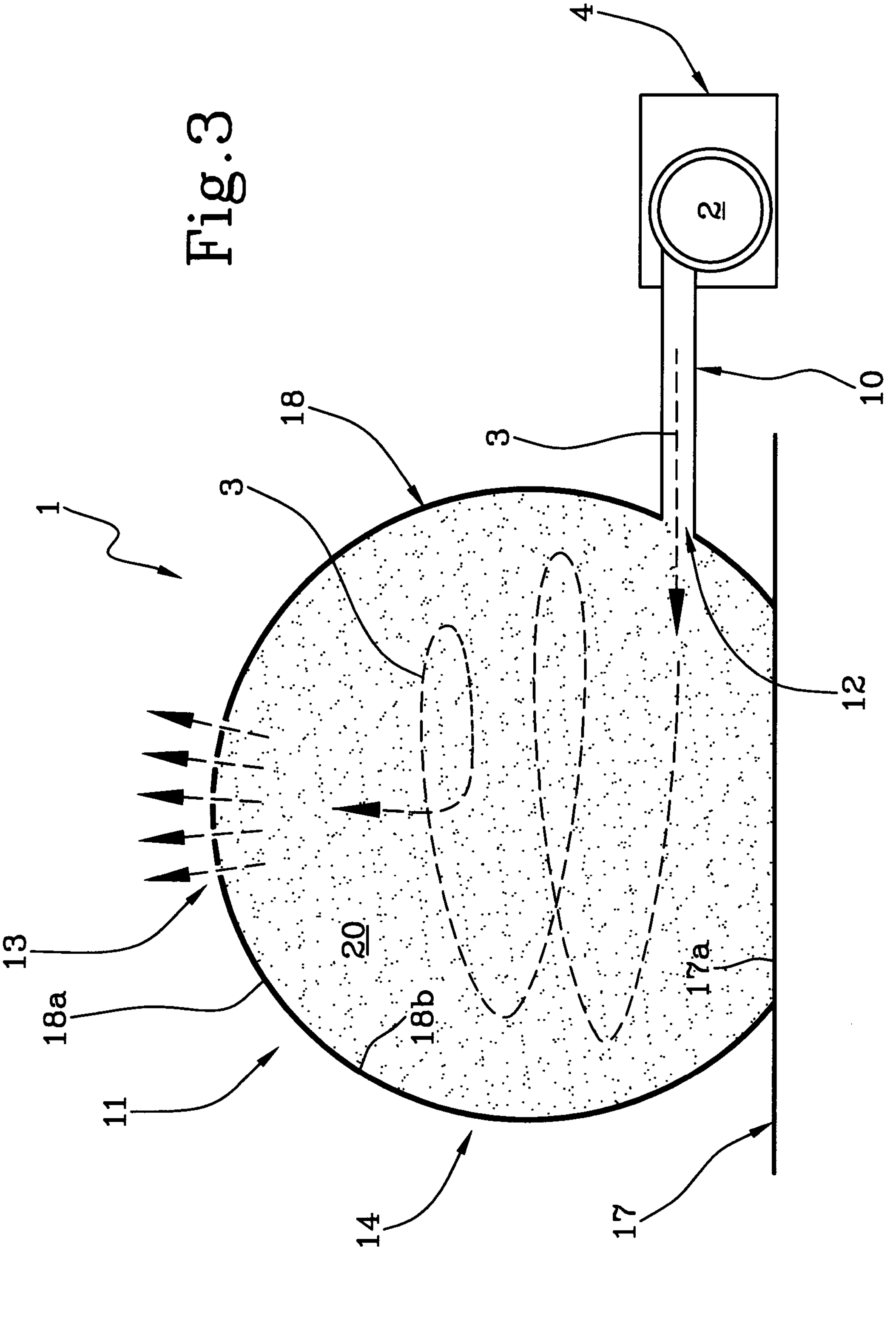
FIG. 3 is a schematized side elevation view of the device of FIG. 1 in the operating condition.

Advantageously, the positioning of the inlet 12 and outlet 13, combined with the spherical conformation of the wall 18, defines a vortex-like path for the air flow inside the space 20 (FIG. 3). This ensures a recirculation of air inside the space 20 from bottom to top and according to a motion surrounding the user. This path has the advantage of avoiding conditions of saturation of the space 20 and of enveloping the user's entire body with the therapeutic mist.

The lateral wall 18 further comprises a slit 19, preferably vertical and provided with a fastening, preferably a zipper, which can be manually switched between an open condition, in which it permits the user to pass from the outside into the space 20 and a closed condition.

The frame 15 preferably comprises two flexible poles 16, respectively perpendicular to each other, and each having an arched profile.

In particular, each pole 16 comprises two opposite ends 16*a* engaged with the base 17 and a top portion 16*b* disposed above the lateral wall 18 in the area of the outlet 13.

In this situation it should be noted that the lateral wall 18 comprises two pairs of tubular bands 21 extending from the outer spherical surface 18*a* of the wall 18 itself. As is better illustrated in FIGS. 1 and 2, each pole 16 passes inside a respective pair of bands 21.

Advantageously, the two poles 16 define vault-like members capable of supporting the lateral wall 18. It should moreover be noted that the top portions 16*b* are respectively superimposed one upon the other and that the opposite ends 16*a* of the poles 16 are associated, according to known coupling methods not described and illustrated in detail, with an area of the upper surface 17*a* of the base 17 outside the accommodating space 20.

As is illustrated in FIG. 1, the poles 16 support the lateral wall 18 and keep it in position when the same is in an operating condition in which it is spherical and is inflated by the air generated by the member 2.

FIG. 2 shows a non-operating condition in which the flow 3 is not dispensed into the space 20 and the lateral wall 18 is deflated. In this condition, even though it does not have a spherical profile, the wall 18 is nonetheless supported by the poles 16 to prevent it from collapsing to the ground, falling, for example, on the user in the event of malfunctioning of the member 2.

Each pole 16 comprises a plurality of segments 22 aligned with one another in the operative condition and a plurality of elastic elements 23 interposed between the segments 22. In particular, as is better illustrated in FIGS. 4 and 5, each elastic element 23 is associated between the ends of two adjacent segments 22.

In this manner, in the operative condition the segments 22 are aligned and held adjacent to each other as a result of the elastic elements 23, whereas in the non-operative condition the segments 22 can be placed alongside each other so as to be disposed parallel (FIG. 4). In this situation the poles 16 are disassembled in a condition of minimum volume so as to be easily put away and contained in the internal area 4*b* (FIG. 5).

Analogously, the body 14 defined by the lateral wall 18 and base 17 can also be folded up (FIG. 4) so as to be switched into the condition of minimum volume in which it can be inserted into the internal area 4*b* of the box-like body 4.

Consequently, in the non-operating condition the entire device 1 can be stored inside the box-like body 4 and is thus advantageously capable of limiting the overall dimensions defined by the structure of the chamber 11.

The present invention further relates to a method for the dispensation of mists for therapeutic use, comprising the steps of: preparing the dispensing member 2, preferably of the above-described type; setting up the chamber 11, and connecting the dispensing member 2 with the chamber 11 via the communication conduit 10 in order to introduce the air flow into said space 20.

The step of setting up the chamber 11 is carried out by switching the chamber 11 itself from a non-operative condition of minimum volume to an operative condition of maximum volume in which it defines the space 20 for containing a user.

In other words, starting from a condition of non-use, the body 14 is unfolded so as to dispose the base 17 with the lower surface 17*b* on the ground.

The frame 15 is subsequently assembled and the body 14 is engaged with the supporting frame 15. The conduit 10 is subsequently engaged with the chamber 18 and the member 2 so as to dispense the air flow 3 into the space 20.

The step of constructing the frame 15 is carried out by aligning the segments 22 associated with each other to define the two poles 16.

Each pair of tubular bands 21 is subsequently fitted over a respective pole 16, the poles 16 being disposed transversely to each other.

The poles 16 are subsequently bent into an arch, maintaining the respective ends 16*a* on the upper surface 17*a* of the base 17. The top portions 16*b* of the poles 16 are positioned one on top of the other and respectively above the body 14.

The step of dispensing the air flow 3 comprises the step of mixing the micronized particles of the therapeutic substance with the air flow generated by the ventilation unit 9 so as to create a mist. This step is carried out in the member 2 contained in the box-like body 4. Consequently, the air flow passing along the conduit 10 is introduced into the lateral wall 18, causing the lateral wall 18 to inflate and define the containment space 20 having a spherical conformation.

The user positioned inside the space 20 is therefore completely enveloped by the mist, to enable both inhalation and a skin treatment.

The above-described invention solves the problems encountered in the prior art and has numerous advantages.

In the first place, the device 1 for the dispensation of mists for therapeutic use is structurally simple and thus has moderate costs and compact dimensions.

It should be noted, in fact, that the chamber 11 can be easily set up in any environment by simply operating on the frame 15 so as to define the poles 16 and by simply unfolding the body 14 that is in the form of a sheet.

Moreover, thanks to the possibility of dismantling and folding up the structure which defines the chamber 11, and inserting it into the box-like body 4, the entire device 1 can be used at any time, has very compact dimensions in the conditions of non-use and above all does not require any fixed structures.

This feature enables the device 1 also to be used in a home environment. What is more, it should be noted that the device 1 entirely replaces the application of masks or devices that are suitable exclusively for dispensation to the respiratory tract. Advantageously, the therapeutic substance is dispensed correctly both to the respiratory tract and the skin, irrespective of the type of user (adult or child).

The invention claimed is:

1. A device for the dispensation of mists for therapeutic use, comprising:

a dispensing member (2) for dispensing an air flow (3) within which micronized particles of a liquid or solid therapeutic substance are dispersed;

a chamber (11) having at least one inlet (12) for said air flow (3) generated by the dispensing member (2) and at least one outlet (13) for said air flow (3) present inside the chamber (11) itself; and a communication conduit (10) interposed between said dispensing member (2) and said chamber (11) in order to introduce the air flow (3) into the chamber (11) itself;

wherein said chamber (11) can be switched between an operative condition of maximum volume in which it internally defines a space (20) for containing at least one user, and a non-operative condition of minimum volume suitable for transport and/or storage;

said chamber (11) comprising a body (14) made of flexible material and in the form of a sheet so as to be folded up in the non-operative condition, and a supporting frame (15), having a plurality of flexible poles (16), which can be folded up in the non-operative condition;

said body (14) comprises a base (17) to be rested on the ground in the operative condition and having an upper rest surface (17*a*) for the user and a lateral wall (18), made in one piece with said base (17), and having an inner surface (18*b*) defining said space (20) for containing at least one user in cooperation with said upper rest surface (17*a*) of the base (17);

wherein said lateral wall (18) has a substantially spherical conformation and said inlet (12) is defined by at least one through opening fashioned in an area of the lateral wall (18) near the base (17), and said outlet (13) is defined by at least one through opening fashioned in an area of the lateral wall (18) that is distal relative to the base (17) and corresponds to the top of the spherical conformation.

2. The device according to claim 1, characterized in that said lateral wall (18) further comprises a slit (19) provided with a zipper that can be switched between an open condition, in which it permits the passage of a user from the outside into the space (20) and a closed condition in which it does not permit said passage.

3. The device according to claim 1, characterized in that said communication conduit (10) comprises a flexible tubular element associated with said through opening defining the inlet (12).

4. The device according to claim 1, characterized in that said air flow (3) extends from the inlet (12) to the outlet (13) along a vortex-like path during use in said operative condition.

5. The device according to claim 3, characterized in that it comprises two respectively perpendicular flexible poles (16), each of which having an arched profile; each pole comprising two opposite ends (16*a*) engaged with said base (17) and a top portion (16*b*) disposed above the lateral wall (18).

6. The device according to claim 5, characterized in that said lateral wall (18) comprises two pairs of tubular sleeves (21) extending from an outer spherical surface (18*a*) of the wall (18) itself; each pole (16) passing inside a respective pair of tubular sleeves (21).

7. The device according to claim 6, characterized in that the top portions (16*b*) of said poles (16) are respectively superimposed one on top of the other and that the opposite ends (16*a*) of the poles (16) are associated with an area of the upper surface (17*a*) of the base (17) outside said containing space (20).

8. The device according to claim 1, characterized in that each pole (16) comprises a plurality of segments (22) that are aligned with one another in the operative condition and a plurality of elastic elements (23) interposed between the segments (22), each of which associated between the ends of two adjacent segments (22); said segments (22) being placeable side by side in the non-operative condition so as to be disposed parallel to each other.

9. The device according to claim 1, characterized in that it further comprises a box-like body (4) for containing said dispensing member (2) and having a through opening through which said communication conduit (10) extends; said communication conduit (10) being made of flexible material that is foldable in a respective non-operative condition.

10. The device according to claim 9, characterized in that said box-like body (4) further comprises an internal area (4*b*) for containing the conduit (10) and the chamber (11) in the respective non-operative conditions of minimum volume.

* * * * *